United States Patent
Song

(10) Patent No.: US 10,610,156 B2
(45) Date of Patent: Apr. 7, 2020

(54) WEARABLE DEVICE

(71) Applicants: Hisense Mobile Communications Technology Co., Ltd., Shandong (CN); Hisense USA Corp., Suwanee, GA (US); Hisense International Co., Ltd., Qingdao, Shandong (CN)

(72) Inventor: Tao Song, Shandong (CN)

(73) Assignees: HISENSE MOBILE COMMUNICATIONS TECHNOLOGY CO., LTD., Qingdao, Shandong (CN); HISENSE USA CORP., Suwanee, GA (US); HISENSE INTERNATIONAL CO., LTD, Qingdao (CN)

( * ) Notice: Subject to any disclaimer, the term of this patent is extended or adjusted under 35 U.S.C. 154(b) by 109 days.

(21) Appl. No.: 15/937,577

(22) Filed: Mar. 27, 2018

(65) Prior Publication Data

US 2018/0214078 A1 Aug. 2, 2018

Related U.S. Application Data

(63) Continuation of application No. PCT/CN2016/074593, filed on Feb. 25, 2016.

(30) Foreign Application Priority Data

Sep. 28, 2015 (CN) .......................... 2015 1 0631135

(51) Int. Cl.
 *A61B 5/00* (2006.01)
 *A61B 5/02* (2006.01)
 (Continued)

(52) U.S. Cl.
 CPC .............. *A61B 5/681* (2013.01); *A61B 5/002* (2013.01); *A61B 5/01* (2013.01); *A61B 5/02* (2013.01);
 (Continued)

(58) Field of Classification Search
 CPC ........... A61B 5/681; A61B 5/002; A61B 5/01; A61B 5/02438
 See application file for complete search history.

(56) References Cited

U.S. PATENT DOCUMENTS

| | | | |
|---|---|---|---|
| 5,638,342 A | 6/1997 | Kartsotis et al. | |
| 2014/0296734 A1 | 10/2014 | Tu et al. | |

(Continued)

FOREIGN PATENT DOCUMENTS

| | | |
|---|---|---|
| CN | 201431031 Y | 3/2010 |
| CN | 102566403 A | 7/2012 |

(Continued)

OTHER PUBLICATIONS

International Search Report for International Application No. PCT/CN2016/074593 dated Jul. 5, 2016; 13 pages (Continued)

*Primary Examiner* — Paula J Stice
(74) *Attorney, Agent, or Firm* — Brinks Gilson & Lione; Yuezhong Feng

(57) ABSTRACT

A wearable device is provided. The wearable device includes a host. A wristband is connected to both sides of the host. A support assembly is connected to a back shell of the host. The support assembly includes a cushion block. The cushion block is a hollow structure. The cushion block is recessed inwardly on a surface of the cushion block toward the back shell of the host to form a groove. The back shell of the host is able to extend into the groove. An elastic member is provided in the groove. One end of the elastic member is connected to the back shell of the host, and another end of the elastic member is connected to a bottom surface of the groove.

16 Claims, 3 Drawing Sheets

(51) Int. Cl.
*A61B 5/01* (2006.01)
*A61B 5/024* (2006.01)
(52) U.S. Cl.
CPC ........ *A61B 5/02438* (2013.01); *A61B 5/6844* (2013.01); *A61B 2562/164* (2013.01)

(56) References Cited

U.S. PATENT DOCUMENTS

2015/0185766 A1   7/2015  Otsuka et al.
2015/0265214 A1   9/2015  De Kok et al.

FOREIGN PATENT DOCUMENTS

| CN | 202589516 U | 12/2012 |
|----|-------------|---------|
| CN | 203465521 U | 3/2014 |
| CN | 103763970 A | 4/2014 |
| CN | 104095622 A | 10/2014 |
| CN | 204192610 U | 3/2015 |
| CN | 104490384 A | 4/2015 |
| CN | 104510456 A | 4/2015 |
| DE | 101 39 749 A1 | 2/2003 |
| WO | WO 2008/134847 A1 | 11/2008 |
| WO | WO 2010/111788 A1 | 10/2010 |

OTHER PUBLICATIONS

First Office Action for International Application No. CN 201510631135.2 dated Jun. 7, 2017; 14 pages.
Second Office Action for International Application No. CN 201510631135.2 dated Dec. 7, 2017; 17 pages.
Objection to the Chinese Patent Family for International Application No. 201510631135.2 dated Mar. 6, 2018; 4 pages.

WEARABLE DEVICE

CROSS-REFERENCE TO RELATED APPLICATION(S)

This application is a Continuation of International Patent Application No. PCT/CN2016/074593, filed Feb. 25, 2016, which claims priority to Chinese Patent Application No. 201510631135.2, filed on Sep. 28, 2015, titled "WEARABLE DEVICE", the entirety of all of which are incorporated by reference herein.

TECHNICAL FIELD

The present disclosure relates to wearable devices, and more particularly, to a wearable device.

BACKGROUND

With the continuous development of science and technology, wearable devices have gradually become intelligent. As a result, smart wristbands, smart watches, smart glasses, smart helmets and other smart wearable devices have emerged. These smart wearable devices are widely used because they can be configured to record vital signs data and make/answer calls.

SUMMARY

Some embodiments of the present disclosure provide a wearable device. The wearable device includes a host. A wristband is connected to both sides of the host. A support assembly is connected to a back shell of the host. The support assembly includes a cushion block. The cushion block is a hollow structure. The cushion block is recessed inwardly on a surface of the cushion block toward the back shell of the host to form a groove. The back shell of the host is able to extend into the groove. An elastic member is provided in the groove. One end of the elastic member is connected to the back shell of the host, and another end of the elastic member is connected to a bottom surface of the groove.

BRIEF DESCRIPTION OF THE DRAWINGS

In order to describe technical solutions in embodiments of the present disclosure more clearly, the drawings to be used in the description of embodiments will be introduced briefly. Obviously, the drawings to be described below are merely some embodiments of the present disclosure, and a person of ordinary skill in the art can obtain other drawings according to those drawings without paying any creative effort.

DETAILED DESCRIPTION

Figure 1:
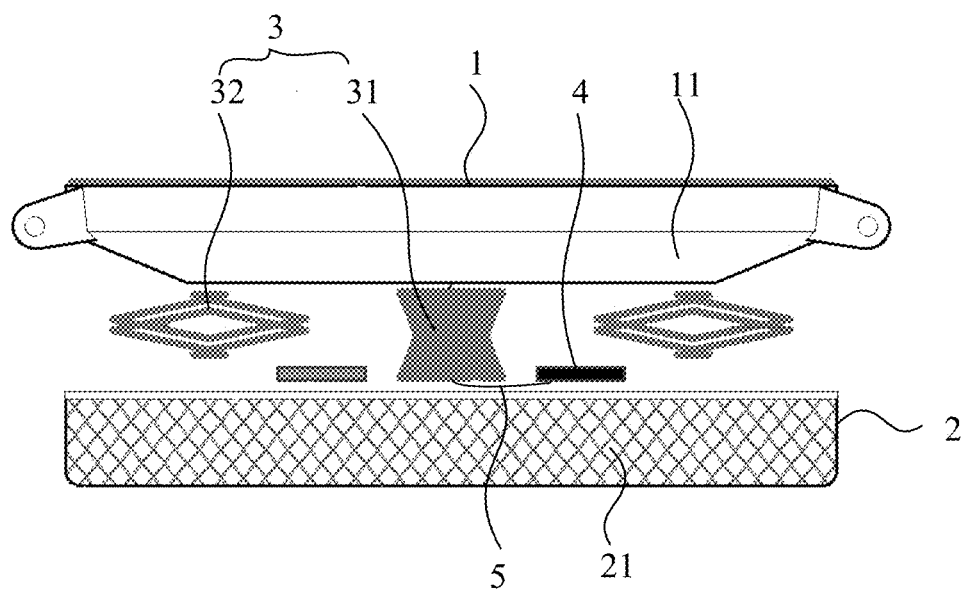
FIG. 1 shows an exploded view of a wearable device according to some embodiments of the present disclosure.

The technical solutions in embodiments of the present disclosure will be described clearly and completely with reference to the drawings in the embodiments of the present disclosure. Obviously, the described embodiments are merely some but not all of embodiments of the present disclosure. All other embodiments made on the basis of the embodiments of the present disclosure by a person of ordinary skill in the art without paying any creative effort shall be included in the protection scope of the present disclosure.

In the description of the present disclosure, it should be understood that, orientations or positional relationships indicated by the terms "center", "upper", "lower", "front", "back", "left", "right", "vertical", "horizontal", "top," "bottom," "inner," "outer," etc. are based on the orientations or positional relationships shown in the drawings and are merely for convenience of describing the present disclosure and simplified the description, but do not indicate or imply that a device or an element referred to must have a particular orientation, be constructed and operated in a particular orientation, and therefore should not be construed to limit the present disclosure.

A wearable device generally refers to a wearable product that can realize powerful functions via software support, data interaction, or cloud interaction. The wearable device generally includes a host. A wristband is provided on both sides of the host. The wristband is used to fix the host to the position attached to a user's skin. The host is generally an integral structure. A surface of the host that is in contact with the user's skin is generally a plane or an arc surface. A control component, a sensing component, a display component and a communication component and the like are provided inside the host. The sensing component is mainly configured to sense vital signs data of the user wearing the wearable device (such as the user's heart rate, body temperature, etc.). Only when the vital signs data of the user is effectively transmitted to the sensing component, a sensitivity of the sensing component can be guaranteed. And when the sensing component can only receive the vital signs data of the user, the accuracy of the sensing component can be ensured.

However, the relative displacement between the above-mentioned integrally molded host and the user's skin easily occurs during the movement of the user. For example, when a side of the host offsets towards a direction away from the user's skin the host or tilted towards one side, the host cannot be effectively attached to the user's skin, and it is difficult to keep a relatively fixed position relationship between the host and the user's skin. In order to fix the relative position between the host and the user's skin, the user may have to further tighten the wristband to improve the compactness between the host and the skin so as to achieve a relative fixation for the host and the user's skin. However, in this way, it is easy to cause a large amount of sweat, a strong feeling of pressure and other uncomfortable conditions appeared on the user's skin.

Referring to FIG. 1, a wearable device according to some embodiments of the present disclosure includes a host 1. A wristband is connected to both sides of the host 1. A support assembly is connected to a back shell 11 of the host 1. The support assembly includes a cushion block 2. The cushion block 2 is a hollow structure. The cushion block 2 is recessed inwardly on a surface of the cushion block 2 toward the back shell 11 of the host 1 to form a groove 21. The back shell 11 of the host 1 is able to extend into the groove 21. An elastic member 3 is provided in groove 21. One end of the elastic member 3 is connected to the back shell 11 of the host 1, and another end of the elastic member 3 is connected to a bottom surface of the groove 21.

In the wearable device according to some embodiments of the present disclosure, since the back shell 11 of the host 1 is connected to the cushion block 2, when the wristband is fastened and a degree of a tightness of the wristband is moderate, the host 1 is fitted to the user's skin via a bottom surface of the cushion block 2. As the cushion block 2 has a structure with groove 21, and the elastic member 3 is provided in the groove 2, one end of the elastic member 3 is connected with the back shell 11 of the host 1, and another end of the elastic member 3 is connected with the bottom surface of the groove 21, when a side of the host 1 offsets towards a direction far away from the user's skin or tilted toward one side, the elastic member 3 is able to still support the cushion block 2, so that the bottom surface of the cushion block 2 is effectively fitted to the user's skin. In this way, the compactness between the host 1 and the user's skin can be improved when the wristband is fastened moderately, which helps the user relieve from experiencing strong press force due to too much tightness of the wristband, and a wearing comfort of the wearing device is improved. In addition, since the cushion block 2 is the hollow structure, outside air flow can enter a part of the cushion block 2 that is in contact with the user's skin, which allows for taking away a part of heat and blowing dry sweats, thereby reducing discomfort of the user's skin caused by sweating.

Figure 2:
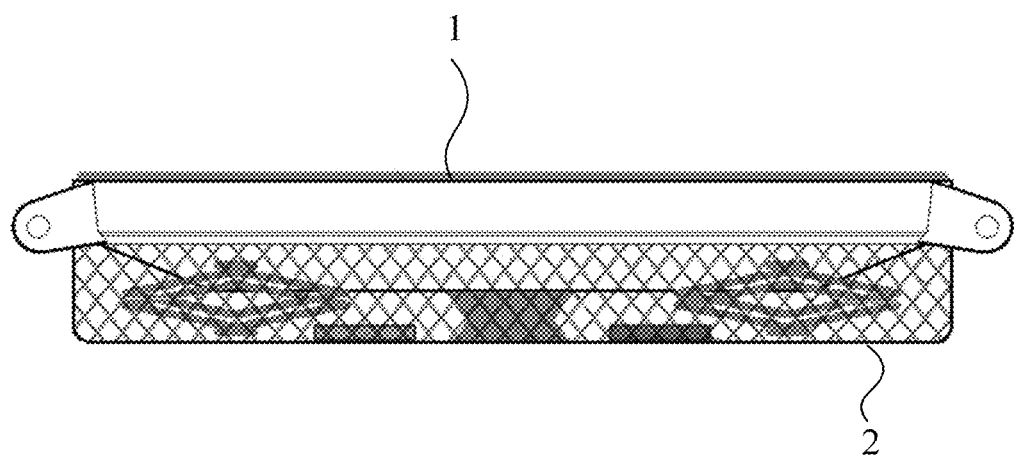
FIG. 2 shows a structural view of a wearable device according to some embodiments of the present disclosure in a compressed state.

In some embodiments of the present disclosure, in order to sense the vital signs data of the user, the sensor 4 is disposed inside the host 1 or the sensor 4 is disposed on the bottom surface of the block 2 as shown in FIG. 2.

When the sensor 4 is disposed inside the host 1, since the back shell 11 of the host 1 is connected to the cushion block 2, the host 1 is in contact with the skin through the bottom surface of the cushion block 2, and the elastic member 3 is disposed in the groove 21 of the cushion block 2, one end of the elastic member 3 is connected to the back shell 11 of the host 1, and another end of the elastic member 3 is connected to the bottom surface of the groove 21, when the bottom surface of the cushion block 2 and the user's skin are fitted, changes of the user's vital signs data (e.g., the heart rate, the body temperature, etc.) are transmitted to the sensor 4 through the cushion block 2, the elastic member 3 and the back shell 11 of the host 1 sequentially, thereby being measured by the sensor 4.

When the sensor 4 is disposed on the bottom surface of the groove 21 of the cushion block 2, and when the bottom surface of the cushion block 2 is in contact with the user's skin, the vital signs data of the user can be transmitted to the sensor 4 through the cushion block 2 and being measured by the sensor 4. In this way, the transmitted path is short and highly reliable, so that a sensitivity of the sensor 4 can be improved.

In some embodiments of the present disclosure, since the control component and the display component of the wearable device are generally provided in the host 1, when the sensor 4 is disposed on the bottom surface of the groove 21, the sensor 4 is electrically connected to the host 1 and transmits the vital signs data of the user sensed by the sensor 4 to the control component in the host 1, and then the control component transmits the vital signs data of the user to the display component connected with the control component to display, thereby it is convenient for the user to view the data.

In some embodiments of the present disclosure, the elastic member 3 includes a main elastic member 31 and one or more elastic limit members 32. Both ends of the main elastic member 31 are connected to the back shell 11 of the host 1 and the bottom surface of the groove 21, respectively. Both ends of one of the one or more elastic limit members 32 are connected to the bottom of the back shell 11 of the host 1 and the groove 21, respectively. When the one of the one or more elastic limit members 32 is compressed to an extreme position, a height of the one of the one or more elastic limit members 32 is greater than a height of the sensor 4. When the wearable device is in a compressed state as shown in FIG. 2, since the height of the one of the one or more elastic limit members 32 is greater than the height of the sensor 4, it is able to effectively prevent the back shell 11 of the host 1 from being in contact with the sensor 4, and thereby avoiding the interference to the sensor 4 caused by the contact between the host 1 and the sensor 4 when the sensor 4 is sensing the vital signs data. In this way, it is able to ensure that the vital signs data detected by the sensor 4 is accurate vital signs data, and thereby improving the accuracy of the sensor 4 in sensing the vital signs data.

In some embodiments of the present disclosure, the bottom surface of the cushion block 2 is designed as a straight surface to simplify the manufacturing process of the wearable device. In other embodiments of the present disclosure, the bottom surface of the cushion block 2 is designed as an arc surface.

Figure 3:
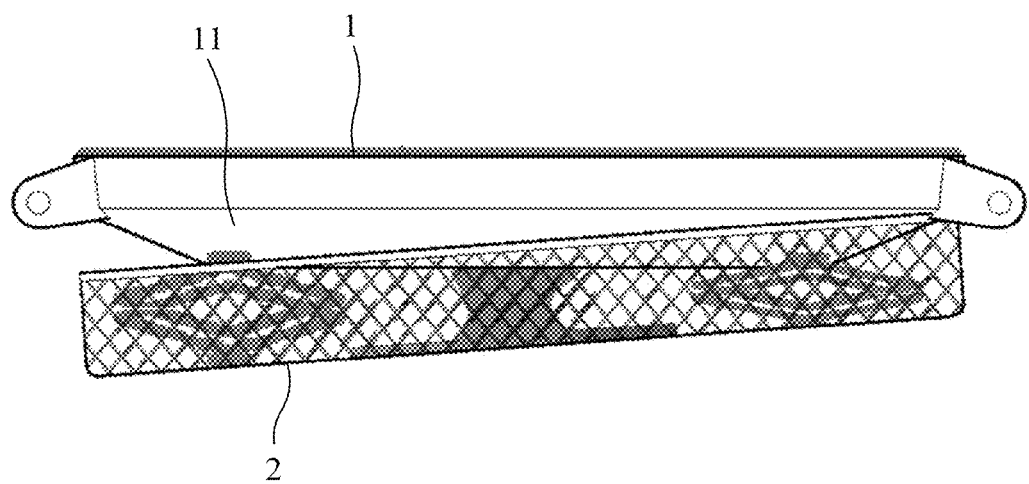
FIG. 3 shows a structural view of a wearable device according to some embodiments of the present disclosure in a tiled and compressed state.

When the bottom surface of the cushion block 2 is a straight surface as shown in FIG. 1 or FIG. 2, since the surface of the user's skin is generally an arc surface in a free state, when the bottom surface of the cushion block 2 is completely fitted to the user's skin, a middle part of the bottom surface of the cushion block 2 is maximally subjected to a extrusion force of the user's skin. Accordingly, in some embodiments of the present disclosure, in order to resist the extrusion force which is maximally subjected by the middle part of the bottom surface of the cushion block 2, the main elastic member 31 is disposed in a middle part of the groove 21, so that the extrusion force which is maximally subjected by the middle part of the bottom surface of the cushion block 2 acts on the main elastic member 31 directly through the groove 21. Therefore, a support of the main elastic member 31 is more stable and stress acting on both sides of the main elastic member 31 is more even. In this way, it is able to effectively avoid that a side of the cushion block 2 is approaching the back shell 11 of the host 1 as shown in FIG. 3 which is caused by uneven stress acting on both sides of the main elastic member 31 and thereby reducing the possibility of the sensor 4 being in contact with the back shell 11 of the host 1 and ensuring the accuracy of the vital signs data sensed by the sensor 4.

Figure 4:
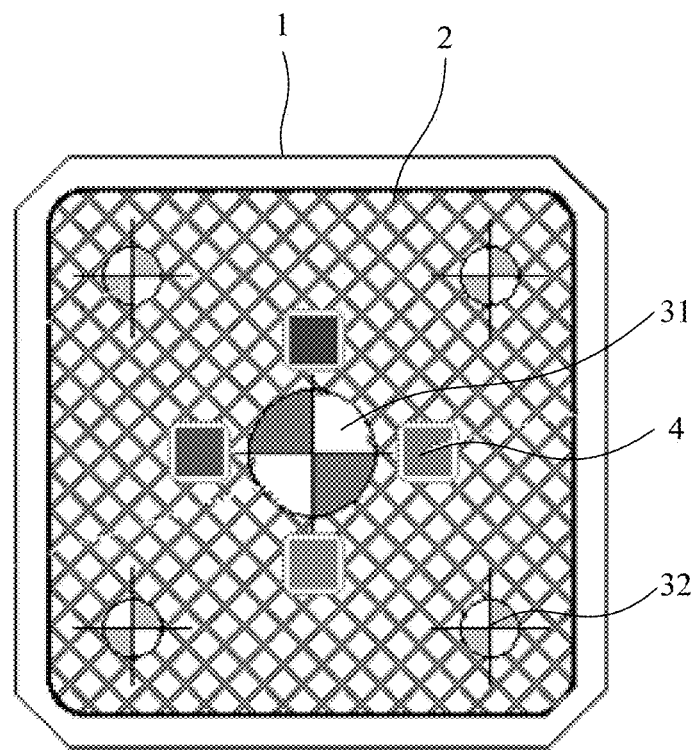
FIG. 4 shows a bottom view of the wearable device shown in FIG. 2.

Further, in some embodiments of the present disclosure, in order to prevent the sensor 4 from being in contact with the back shell 11 of the host 1, the sensor 4 is disposed in a position adjacent to the main elastic member 31, and the elastic member 3 includes a plurality of elastic limit members 32 disposed at the edge of the groove 21, as shown in FIG. 4. In this way, it is able to define a minimum distance between the back shell 11 of the host 1 and the bottom of the groove 21, so that the distance between a part of the bottom of the groove 21 corresponding to the sensor 4 and the back shell 11 of the host 1 is greater than the minimum distance. Furthermore, since the height of one of the plurality of elastic limit member 32 when it is compressed to the extreme position is greater than the height of the sensor 4, it is able to ensure that the distance between the part of the bottom of the groove 21 corresponding to the sensor 4 and the back shell 11 of the host 1 is greater than the height of the sensor 4, and thereby effectively preventing the sensor 4 from being in contact with the back shell 11 of the host 1 and ensuring the accuracy of the sensor 4.

The number of the plurality of elastic limit members 32 may be 2, 3, 4 or 5, and so on. With the increase in the number of the plurality of elastic limit members 32, the difficulties in manufacturing the wearable device are increased, and the manufacturing costs are increased. Therefore, referring to FIG. 4, the number of the plurality of elastic limit members 32 is set to be four and the plurality of elastic limit members 32 are uniformly distributed at the edge of the groove 21, so that the plurality of elastic limit members 32 are distributed in four directions around the main elastic member 31. In this way, it is able to prevent the back shell 11 of the host 1 from being in contact with the sensor 4 in all directions, and thereby ensuring the accuracy of sensing, under the premise of ensuring less manufacturing difficulties and lower manufacturing costs.

Figure 5:
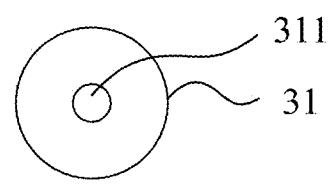
FIG. 5 shows a top view of a main elastic member in a wearable device according to some embodiments of the present disclosure.

In some embodiments of the present disclosure, the sensor 4 and the host 1 are electrically connected by a wire 5 as shown in FIG. 1. The wire 5 is directly disposed in a space of the groove 21 of the cushion block 2, or is disposed inside the main elastic member 31. When the wire 5 is disposed inside the main elastic member 31, and the main elastic member 31 is manufactured as the structure as shown in FIG. 1, a through hole 311 is provided in a middle part of the main elastic member 31, one end of the wire 5 is connected to the host 1, and another end of the wire 5 is passed through the through hole 311 and connected to the sensor 4, as shown in FIG. 5. The main elastic member 31 blocks out water, dust and the like in the external environment, and thus ensuring the safety of the current conduction in the wire 5. The guide wire 5 is disposed inside the main elastic member 31, and thus ensuring the consistence of the appearance of the wearable device. The main elastic member 31 is a member having elasticity. The main elastic member 31 is a spring or a rubber pad. Both of the spring and the rubber pad are common and inexpensive.

Figure 6:
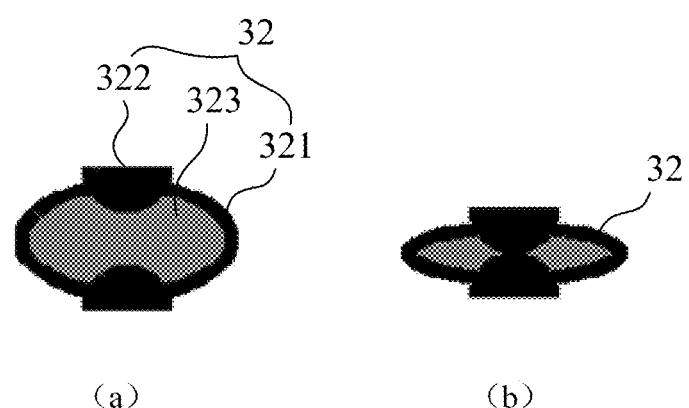
FIG. 6 shows a structural view of an elastic limit member in a wearing device according to some embodiments of the present disclosure in a free state and a compressed extreme state, wherein, (a) is a structural view of the elastic limit member in the free state, and (b) is a structural view of the elastic limit member in the compressed extreme state.

In some embodiments of the present disclosure, one of the one or more elastic limit members 32 is manufactured as the structure as shown in FIG. 6(a). That is, one of the one or more elastic limit members 32 includes an outer shell 321 made of an elastic material. An inner cavity is provided inside the outer shell 321. An upper end and a lower end of the outer shell 321 are connected to the back shell 11 of the host 1 and the bottom of the groove 21, respectively. Protrusions 322 extending into the inner cavity is provided at the upper end and the lower end of the outer shell 32, respectively. The protrusions 322 respectively located at the upper end and the lower end of the outer shell 321 are located along a same straight line and spaced apart. When the one or more the elastic limit members 32 are compressed to the extreme position, tops of the protrusions 322 respectively located at the upper end and the lower end of the outer shell 321 are in contact with each other as shown in (b) of FIG. 6. The height of one of one or more elastic limit members 32 that is compressed to the extreme position is equal to a sum of the heights of the protrusions 322 respectively located at the upper end and the lower end of the outer shell 321. The sum of the heights of the protrusions 322 respectively located at the upper end and the lower end of the outer shell 321 is greater than the height of the sensor 4. This structure is simple and easy to implement.

In some embodiments of the present disclosure, in order to make the one or more elastic limit members 32 have a certain elastic force, an elastic material 323 such as a soft rubber ball or the like is filled in the inner cavity of the outer shell 321 and the degree of difficulty of deforming the one or more elastic limit members 32 is adjusted according to the amount and the kind of the elastic material 323 filled in the inner cavity of the outer shell 321. When the one or more elastic limit members 32 are pressed, the elastic material 323 can consume an impact energy between the protrusions 322 respectively located at the upper end and the lower end of the outer shell 321, so as to prevent the tops of the protrusions 322 from being incomplete due to too much impact force between the protrusions 322 located at the upper end and the lower end of the outer shell 321 respectively. In this way, it is able to further prevent the sum of the heights of the protrusions 322 respectively located at the upper end and the lower end of the outer shell 321 from becoming smaller, and thereby reducing the possibility that the back shell 11 of the host 1 is in contact with the sensor 4.

The above descriptions are merely specific embodiments of the present disclosure, but the protection scope of the present disclosure is not limited thereto. A person of ordinary skill in the art can easily conceive changes or replacements within the technical scope disclosed by the present disclosure, and the changes or the replacements should all fall within the protection scope of the present disclosure. Therefore, the protection scope of the present disclosure should be based on the protection scope of the claims.

What is claimed is:

1. A wearable device, comprising:
   a host which includes a control component, a display component and a communication component;
   a support assembly connected to a back shell of the host, and the back shell being close to a wearer in a case where the wearer wears the wearable device, wherein the support assembly comprises:
      a cushion block with a hollow structure, the cushion block is recessed inwardly on a surface of the cushion block toward the back shell of the host to form a groove, and the back shell of the host is able to extended into the groove; and
      an elastic member provided in the groove, with one end connected to the back shell of the host and another end connected to a bottom surface of the groove;
   a sensor provided at the bottom surface of the groove, wherein the sensor is configured to sense the vital signs data of the wearer, and the sensor is electrically connected to the host.

2. The wearable device according to claim 1, wherein the elastic member comprises a main elastic member and one or more elastic limit members, wherein:
   one end of the main elastic member is connected to the back shell of the host and another end to the bottom surface of the groove; and
   one end of one of the one or more elastic limit members is connected to the back shell of the host and another end of the one of the one or more elastic limit member is connected to the bottom surface of the groove, and a height of the one of the one or more elastic limit members when compressed to an extreme position is greater than a height of the sensor.

3. The wearable device according to claim 2, wherein:
   the main elastic member is located in a middle part of the groove; and the elastic member comprises a plurality of elastic limit members, and the plurality of elastic limit members are distributed at an edge of the groove.

4. The wearable device according to claim 3, wherein a number of the plurality of elastic limit members is four, and the plurality of elastic limit members are uniformly distributed at the edge of the groove.

5. The wearable device of claim 2, wherein the sensor and the host are electrically connected via a wire; and
a through hole is provided in a middle part of the main elastic member, one end of the wire is connected to the host, and another end of the wire is passed through the through hole and connected to the sensor.

6. The wearable device according to claim 2, wherein the main elastic member is a spring or a rubber pad.

7. The wearable device according to claim 2, wherein one of the one or more elastic limit member comprises:
an outer shell made of an elastic material, an upper end of the outer shell is connected to the back shell of the host and a lower end of the outer shell is connected to the bottom surface of the groove;
an inner cavity provided inside the outer shell; and
protrusions extending into the inner cavity provided at the upper end and the lower end of the outer shell, respectively, and a protrusion located at the upper end and another protrusion at the lower end of the outer shell are located along a same straight line and spaced apart.

8. The wearing device of claim 7, wherein the inner cavity is filled with an elastic material.

9. A wearable device, comprising:
a host;
a support assembly connected to a back shell of the host, wherein the support assembly comprises:
a cushion block with a hollow structure, the cushion block is recessed inwardly on a surface of the cushion block toward the back shell of the host to form a groove, and the back shell of the host is able to extended into the groove; and
an elastic member provided in the groove, with one end connected to the back shell of the host and another end connected to a bottom surface of the groove;
a sensor provided at the bottom surface of the groove; wherein the sensor is electrically connected to the host via a wire;
wherein the elastic member comprises a main elastic member and one or more elastic limit members, wherein:
one end of the main elastic member is connected to the back shell of the host and another end to the bottom surface of the groove; and
one end of one of the one or more elastic limit members is connected to the back shell of the host and another end of the one of the one or more elastic limit member is connected to the bottom surface of the groove, and a height of the one of the one or more elastic limit members when compressed to an extreme position is greater than a height of the sensor;
wherein the sensor and the host are electrically connected via a wire; and
a through hole is provided in a middle part of the main elastic member, one end of the wire is connected to the host, and another end of the wire is passed through the through hole and connected to the sensor.

10. The wearable device according to claim 9, wherein:
the main elastic member is located in a middle part of the groove; and
the elastic member comprises a plurality of elastic limit members, and the plurality of elastic limit members are distributed at an edge of the groove.

11. The wearable device according to claim 10, wherein a number of the plurality of elastic limit members is four, and the plurality of elastic limit members are uniformly distributed at the edge of the groove.

12. The wearable device according to claim 9, wherein the main elastic member is a spring or a rubber pad.

13. A wearable device, comprising:
a host;
a support assembly connected to a back shell of the host, wherein the support assembly comprises:
a cushion block with a hollow structure, the cushion block is recessed inwardly on a surface of the cushion block toward the back shell of the host to form a groove, and the back shell of the host is able to extended into the groove; and
an elastic member provided in the groove, with one end connected to the back shell of the host and another end connected to a bottom surface of the groove;
a sensor provided at the bottom surface of the groove, wherein the sensor is electrically connected to the host;
wherein the elastic member comprises a main elastic member and one or more elastic limit members, wherein:
one end of the main elastic member is connected to the back shell of the host and another end to the bottom surface of the groove; and
one end of one of the one or more elastic limit members is connected to the back shell of the host and another end of the one of the one or more elastic limit member is connected to the bottom surface of the groove, and a height of the one of the one or more elastic limit members when compressed to an extreme position is greater than a height of the sensor;
wherein one of the one or more elastic limit member comprises:
an outer shell made of an elastic material, an upper end of the outer shell is connected to the back shell of the host and a lower end of the outer shell is connected to the bottom surface of the groove;
an inner cavity provided inside the outer shell; and
protrusions extending into the inner cavity provided at the upper end and the lower end of the outer shell, respectively, and a protrusion located at the upper end and another protrusion at the lower end of the outer shell are located along a same straight line and spaced apart.

14. The wearable device according to claim 13, wherein:
the main elastic member is located in a middle part of the groove; and
the elastic member comprises a plurality of elastic limit members, and the plurality of elastic limit members are distributed at an edge of the groove.

15. The wearable device according to claim 14, wherein a number of the plurality of elastic limit members is four, and the plurality of elastic limit members are uniformly distributed at the edge of the groove.

16. The wearable device according to claim 13, wherein the main elastic member is a spring or a rubber pad.

* * * * *